(12) United States Patent
Clarke et al.

(10) Patent No.: US 9,818,285 B2
(45) Date of Patent: *Nov. 14, 2017

(54) METHOD AND APPARATUS FOR MOVING WHILE RECEIVING INFORMATION

(71) Applicants: James Clarke, Washington, DC (US); Chiedo Ohanyerenwa, Washington, DC (US)

(72) Inventors: James Clarke, Washington, DC (US); Chiedo Ohanyerenwa, Washington, DC (US)

(73) Assignee: Forward Entertainment & Technology, LLC, Washington, DC (US)

( * ) Notice: Subject to any disclaimer, the term of this patent is extended or adjusted under 35 U.S.C. 154(b) by 446 days.

This patent is subject to a terminal disclaimer.

(21) Appl. No.: 14/217,508

(22) Filed: Mar. 18, 2014

(65) Prior Publication Data
US 2014/0190789 A1 Jul. 10, 2014

Related U.S. Application Data

(60) Provisional application No. 61/786,840, filed on Mar. 15, 2013.

(51) Int. Cl.
| | |
|---|---|
| *G08B 21/18* | (2006.01) |
| *B29D 23/00* | (2006.01) |
| *B66B 3/00* | (2006.01) |
| *F16L 11/10* | (2006.01) |
| *F16L 11/12* | (2006.01) |
| *A61B 5/11* | (2006.01) |

(Continued)

(52) U.S. Cl.
CPC ............ *G08B 21/18* (2013.01); *A61B 5/1118* (2013.01); *A61B 5/222* (2013.01); *A61B 5/486* (2013.01); *A61B 5/4833* (2013.01); *B29D 23/00* (2013.01); *B66B 3/002* (2013.01); *F16L 11/10* (2013.01); *F16L 11/12* (2013.01)

(58) Field of Classification Search
None
See application file for complete search history.

(56) References Cited

U.S. PATENT DOCUMENTS 3,281,964 A * 11/1966 Hewes ..................... B64G 7/00
                                                434/34
5,591,104 A * 1/1997 Andrus ................ A61B 5/6887
                                                434/247

(Continued)

*Primary Examiner* — Sunit Pandya
(74) *Attorney, Agent, or Firm* — Forward Entertainment & Technology, LLC; James Lowell Ramsey Clarke; Chiedo Raymond Ohanyerenwa (57) ABSTRACT

A method and apparatus to facilitate learning while moving, efficient multitasking involving movement while the user processes or responds to different stimuli. The stimuli may include but are not limited to information related to education or entertainment or feedback concerning the user's movement. More specifically this movement may be related to coordination, exercise or physiotherapy. The methods and apparatuses of the disclosure involve the user conducting movement, while simultaneously processing information (via: learning; creating through typing, moving, or talking; or being entertained) and receiving feedback or assistance related to that movement, processing, or any combination thereof.

18 Claims, 8 Drawing Sheets

(51) Int. Cl.
 *A61B 5/00* (2006.01)
 *A61B 5/22* (2006.01)

(56) References Cited

U.S. PATENT DOCUMENTS

| | | | | |
|---|---|---|---|---|
| 5,984,839 A * | 11/1999 | Corkum | ............. | A63B 71/0622 |
| | | | | 482/4 |
| 6,458,060 B1 * | 10/2002 | Watterson | ............ | A63B 21/005 |
| | | | | 482/4 |
| 6,902,513 B1 * | 6/2005 | McClure | ............ | A63B 24/0006 |
| | | | | 482/4 |
| 7,044,891 B1 * | 5/2006 | Rivera | ............... | A63B 21/0053 |
| | | | | 482/1 |
| 8,939,831 B2 * | 1/2015 | Dugan | .................. | A63F 13/212 |
| | | | | 463/31 |
| 8,992,383 B2 * | 3/2015 | Bilang | .................... | A63B 22/02 |
| | | | | 482/1 |
| 9,358,422 B2 * | 6/2016 | Brontman | .......... | A63B 22/0023 |
| 9,367,668 B2 * | 6/2016 | Flynt | .................. | A63B 24/0087 |
| 2003/0017913 A1 * | 1/2003 | Stewart | .................. | A63B 22/00 |
| | | | | 482/8 |
| 2006/0205566 A1 * | 9/2006 | Watterson | ............... | A63B 22/00 |
| | | | | 482/8 |
| 2007/0060451 A1 * | 3/2007 | Lucas | .................... | A61H 7/001 |
| | | | | 482/54 |
| 2012/0237911 A1 * | 9/2012 | Watterson | .......... | A63B 24/0087 |
| | | | | 434/247 |
| 2013/0288223 A1 * | 10/2013 | Watterson | ............... | G09B 19/00 |
| | | | | 434/428 |
| 2014/0190789 A1 * | 7/2014 | Clarke | .................... | B66B 3/002 |
| | | | | 198/321 |

* cited by examiner

METHOD AND APPARATUS FOR MOVING WHILE RECEIVING INFORMATION

CROSS-REFERENCE TO RELATED APPLICATION

This application claims the benefit of U.S. Provisional Application No. 61/786,840 filed Mar. 15, 2013. The entire disclosure of U.S. Provisional Application No. 61/786,840 is incorporated herein by reference.

TECHNICAL FIELD

The general field of the disclosure herein relates to methods or apparatuses involving movement to facilitate learning while moving, efficient multitasking involving movement while the user processes or responds to different stimuli. The stimuli may include but are not limited to information related to education or entertainment or feedback concerning the user's movement. More specifically this movement may be related to coordination, exercise or physiotherapy. The methods and apparatuses of the disclosure involve the user conducting movement, while simultaneously processing information (via: learning; creating through typing, moving, or talking; or being entertained) and receiving feedback or assistance related to that movement, processing, or any combination thereof.

BACKGROUND

Studies related to multitasking have shown that people typically process one task less efficiently when coupled with other tasks (see, e.g., "Cognitive Control in Media Multitaskers" by Ophir and Wagner, Proceedings of the National Academy of Sciences of the United States of America, 2009). Ophir and Wagner found that media related multitasking was distinct from normal multitasking and caused users switching between activities to perform worse than during normal multitasking. Terms such as cognitive distraction, distracted driving, distracted walking, visual distraction, and manual distraction describe the ways in which people lose focus or the ability to provide a timely response to a situation to which they would otherwise be able to respond, due to an additional task.

Conversely, studies have shown that movement can stimulate the functionality of the brain, (see, e.g., "Exercise and the brain: something to chew on" by Van Praag, National Institute of Health, Trends in Neuroscience, 2009). Van Praag finds that optimal maintenance and brain health may depend on exercise and intake of natural products. Furthermore feedback and assistance while multitasking can be used to stimulate better coordination of movement and any additional tasks. The benefits of movement related to coordination, exercise, and physiotherapy are numerous, including stimulated muscle memory and reflexes due to repetitive movements involving hand-eye coordination, improved health due to weight loss or lowered blood pressure, increased longevity, restoration of function and movement, and the treatment, healing, and prevention of injuries or disabilities. Studies show that increasing numbers of people are living sedentary lifestyles (See e.g. "Amount of Time Spent in Sedentary Behaviors in the United States, 2003-2004" by Charles E. Matthews et. al., American Journal of Epidemiology, 2008). In his study, Matthews found evidence that most Americans, both male and female over the ages of 6-11 now spend over 50% of their time in sedentary behaviors. This is at least partially related to the drawbacks of the information age, in which many people learn, create or conduct business, or are entertained all from a stationary position while observing monitors on their televisions and computers.

While inventions exist that allow movement while creating such as the laptop computer, movement while reading or learning such as tablet processors, or movement while being entertained such as virtual reality headsets like the Vuzix wrap 230 eyewear product, none of these devices are designed specifically for use while moving, and none of them are designed to provide feedback to the user or assistance to the user specifically related to that movement. A method or apparatus specifically designed to allow the user to process information by learning, creating, or being entertained; while moving through coordination, exercise, or physiotherapy; and that aids the user by providing feedback or assistance related to that movement, processing, or any combination thereof; has the potential of being a boon to society.

SUMMARY OF THE INVENTION

Embodiments of the disclosure herein may refer to methods and apparatus including but not limited to users conducting tasks such as learning, working, creating on a computer or other device, or being engaged in a simulation all while moving and outputting sensory information related to those tasks, their movement, or both to one or more devices. Sensory information collected by those devices may include but is not limited to any audio, visual, or tactile information, which may relate to the users actions or inactions in performing those tasks or in moving. That information may be sent from those devices, herein referred to as sensor relays, to any number of other devices, including but not limited to other sensor relays, one or more computer processors, one or more movement devices. The sensor relay may instead output the information to an output device which converts the information into a form that the user or an observer understands. If the information is received by a computer processor, the computer processor may analyze the information against a set of predetermined set points before sending output information to other devices including but not limited to output devices and movement devices. Movement devices may include any device designed to facilitate the user's movement, including but not limited to treadmills or moving platforms, bicycles, elliptical machines, cable row machines, automatically adjustable weight devices. When receiving a signal from the computer processor, signal relay, or a user or observer who has received feedback regarding the user's sensory information, the movement device may respond accordingly.

One example of an embodiment of this disclosure may be an apparatus containing sensor relays, a treadmill and a headset, all ergonomically designed to transmit signals such that the user receives information while using the treadmill regarding her performance through the headset while simultaneously utilizing the headset to listen to a lecture. Another example may be a treadmill which communicates with a Bluetooth headset so that a microphone in the headset acts as a sensor relay which wirelessly transmits signals to the treadmill indicating when the user is out of breath, thereby causing the treadmill to slow. Additionally, the treadmill may include a sensor relay which transmits a signal to the headset wirelessly indicating the users pace has slowed. A processor may determine that the rate of simulation presented to the user from the headset should be altered. Another example may be a treadmill designed in an adjustable elliptical shape which has sensor relays located along its handle bars to sense the users position, and relays the users position to an observer's output device, who may then choose to remotely alter the speed of the treadmill. Yet another embodiment may be a user with a visual headset on their face acting as an output device and a sensor relay on their leg. The sensor relay may indicate when the user has exited a perimeter marked by electromagnetic signals sent between other sensor relays located at the boundaries of the perimeter. The sensor relay would then send one or more signals to the users visual headset interrupting the movie the user was watching on it to tell them they are outside of a designated safe pacing zone.

It is envisioned that this invention may be used to help users engage in movement while effectively processing information related to their tasks. When executed correctly, the users multitasking may be assisted by this system of devices.

While the preferred embodiments of the invention are shown in the accompanying drawings, it is still to be understood that said embodiments are susceptible to modification and alteration while still maintaining the spirit of my invention.

BRIEF DESCRIPTION OF THE DRAWINGS

Referring to the drawings.

DETAILED DESCRIPTION

In this disclosure the term 'sensor relay' refers to an apparatus composed of any or any combination of devices including but not limited to sensors (including an audio sensor, a visual sensor, a tactile sensor, a gyroscope, an accelerometer, proximity device, or a magnetometer) and relays for sending information such as sensory information or positional information. Sensor relays may include an input or output relays, or any combination therein which may send or receive a signal from the user, an observer, any extension of the user, computer processor or any other sensor relay.

The computer processor is a device which may receive, process, store, or transmit information. The sensor relay may send a signal to the computer processor, another sensor relay, an output device, or a movement device. The computer processor may receive the information from a variety of sources including but not limited to the sensor relays, movement devices, output devices, media devices or any combination thereof. The computer processor may then process the information in a number of different ways including but not limited to analyzing it comparatively against a set point or combination of set points.

Set points are permanent or adjustable values of attributes that may be predefined by individuals, including but not limited to a user, an observer, or a manufacturer. The computer processor may send a signal or combination of signals to a variety of devices including but not limited to other computer processors, sensor relays, output devices, movement device, or media devices.

The output device is a device that may include a computer processor which receives information from a source, including but not limited to a sensor relay or computer processor. The output device may then convert or convey this information, or any combination therein to the user or an observer through any of multiple means, including but not limited to headphones, speakers, a visual monitor or by controlling a movement device. The output device may be or may include a media device.

The media device may have a processor which receives and outputs information as media information. Media information may include learning material (including but not limited to either audio or visual lectures, quizzes, or books) entertainment material (including but not limited to movies, music, or video games), or simulation material (including but not limited to computing material, material directly related to the users movement for physiotherapy, or exercise assistance material). The media device may adjust its rate of output of media information if directed to do so by it's processor. The media device's processor may receive information from a variety of sources including but not limited to users, observers, computer processors, output devices, or sensor relays.

Any signal sent from a sensor relay, computer processor, output device or media device to another can be sent by means including but not limited to wired means (including but not limited to coaxial, vga, hdmi, component, composite, fiber optic, or dvi cables) or wireless means (including but not limited to bluetooth, wifi, or infrared or other electromagnetic waves). Any signal sent from an output device to either a user, observer, any extension of the user or any sensor relay may be sent via means including but not limited to visual, audio, or tactile means.

In some embodiments where it receives signals, the sensor relay may include audio sensors that can receive input from the user or an observer related to sounds that they make, purposely or otherwise. The audio sensor may be comprised of a variety of audio devices including but not limited to microphones or vibration monitors.

In other embodiments the sensor relay may include visual sensors that can detect movement including but not limited to movement of the user's body, any body parts, extensions of the user's body, or eyes (including but not limited to pupil dilation, eye-crossing, eye wiggles, rapid-eye movement, or normal eye movement). The visual sensor may be comprised of a variety of video devices including but not limited to cameras or optical sensors.

In other embodiments the sensor relay may include tactile sensors which may sense contact (including but not limited to touching, depressing or hitting) or changes in contact (including but not limited to grip modulation, sweating, altered breathing, altered pulse, shaking or swiping) that any part of the user's body, observer's body, or extensions of their bodies (including but not limited to clothes, gloves, or any object directly connected to them) or any combination thereof makes with the sensor or any extension connected to the sensor via wired or wireless means.

In other embodiments the sensor relay may include a gyroscope which may detect changes in the location of one body part or extension of body part in relation to another or from its original position, such as but not limited to those indicating alterations in balance, angular velocity, angular momentum, spin, inertia, or torque. In other embodiments the sensor relay may include an accelerometer which may detect the user's average speed, velocity, or any changes therein. In other embodiments the sensor relay may include a magnetometer which may detect changes in magnetization or proximity of a magnetized object connected to the user or any extension of the user.

A movement device may include but is not limited to devices used to facilitate movement or exercise such as a treadmill, bicycle, cable-row, or elliptical machine. In certain embodiments of the disclosure users, observers, sensor relays or computer processors may direct the movement device to alter its settings, including but not limited to its velocity, resistance, incline, or pressure.

Figure 1:
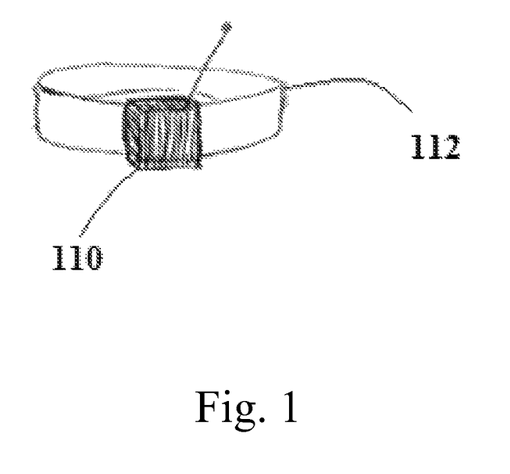
FIG. 1 illustrates an orthogonal view of a portion of an embodiment of the disclosure wherein a relay used for transmitting information regarding the user's movement is transmitted.

In one embodiment of the disclosure a sensor relay, 110, may be attached to a strap, 112, as signals are sent or received by the sensor relay.

Figure 2:
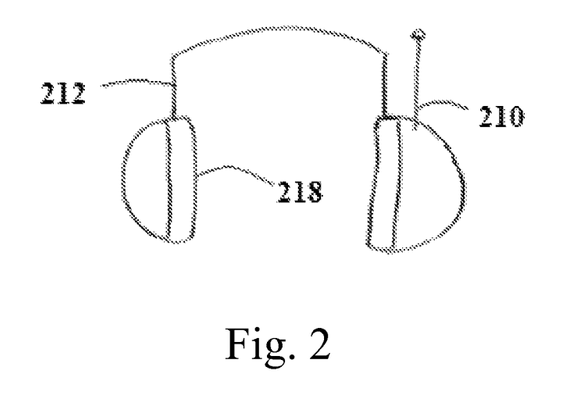
FIG. 2 illustrates a front view of an embodiment of a sensor relay and output device assembly.

In another embodiment of the disclosure a sensor relay, 210, may be wired, 212, and sends signals to an output device, in this case an audio speaker, 218.

Figure 3:
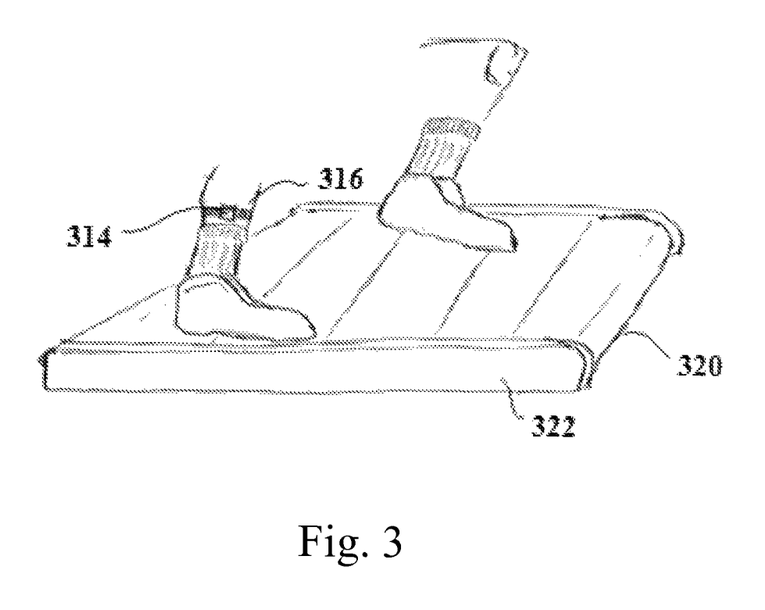
FIG. 3 illustrates an orthogonal view of the relay used for transmitting information regarding the user's movement in position on a human leg in motion on a treadmill or moving walkway.

In another embodiment of the disclosure a sensor relay, 314, may be fitted to a user's calf, 316. In this embodiment the sensor relay may transmit information about the user's movement, and thereby control a track, 320, on a treadmill, 322, while the user is on said treadmill. However other iterations of the disclosure do not require the user to be on a moving device or the moving device can be non treadmill moving devices including but not limited to a moving walkway, bicycle, elliptical, track-pad or cable-row.

Figure 4:
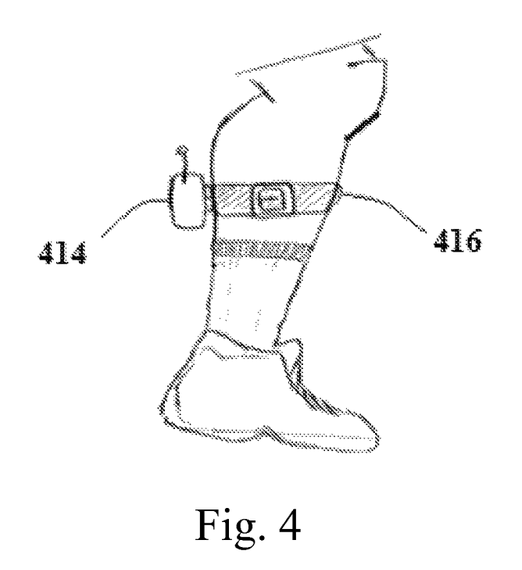
FIG. 4 illustrates an embodiment in which a user's leg movement is detected by a sensor relay.

In another embodiment of the disclosure a sensor relay, 414, may be fitted to the user's calf, 416, although the user is walking on the ground and the sensor relay sends or receives information concerning the users proximity to nearby objects to an output device. However other iterations of the disclosure do not require the sensor relay to include a proximity monitor. Sensor relays in this application can be devices including but not limited to accelerometers, audio sensors, tactile sensors, or gyroscopes.

Figure 5:
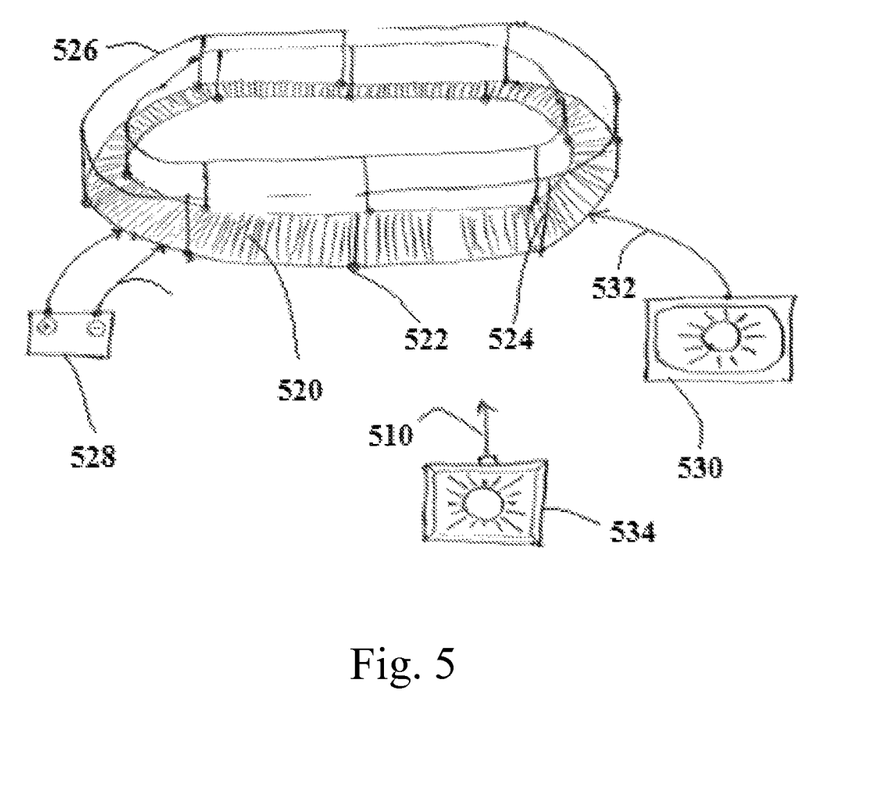
FIG. 5 illustrates an orthogonal view of an embodiment comprising a circular treadmill, one or more solar relays, and battery backup power to supply the treadmill with energy collected from the solar panels or kinetic energy from the user's movement.

Another embodiment of the disclosure may involve a sensor relay, 510, sending signals to a motion device, 520, in the form of a treadmill or moving walkway, 522, which has a circular or elliptical shape. The track the user moves on is in a shape that allows the user to traverse it from beginning to end without fear of going off the track. This has the advantage of allowing the user's speed to significantly differ from the treadmill's speed, without the user having to run into a portion of the treadmill or fall off of the treadmill. Another advantage to this design is that it allows the user more flexibility in movement than a standard treadmill.

In some embodiments the movement of the user may be assisted by: signals sent by the signal relays; a physical guide including but not limited to: supports, 524, which support handle bars, 526; an observer, who receives signals and guides the user; or any combination thereof. In other embodiments the user receives no external assistance in traversing the track, but can effectively traverse in the direction of the track through their own means including but not limited to muscle memory, observation, or mental memory.

Additional embodiments of the disclosure may include a dc battery, 528, powering a device, in this case a circular treadmill. In some embodiments the battery may be rechargeable, and in others it may even be synergistically charged by the user's dispensed kinetic energy. In another embodiment the movement device is powered by a solar panel, 530, which can alternatively be used to power the media device, via wires, 532.

In variations of this embodiment, instead of a circular treadmill, the movement device may be any exercise or entertainment equipment including but not limited to a standard treadmill, bicycle, elliptical, a motorized rocking chair, a track-pad which senses the users location and movements on the pad, or a chair powered by electricity for the purposes of movement or audio output through its embedded speakers or any combination of such devices. The use of rechargeable or portable energy in these embodiments of the disclosure is useful for assisting in maintaining the energy needed to power the device(s) the user is operating, any Signal Relays, computer processors or combinations thereof.

Figure 6:
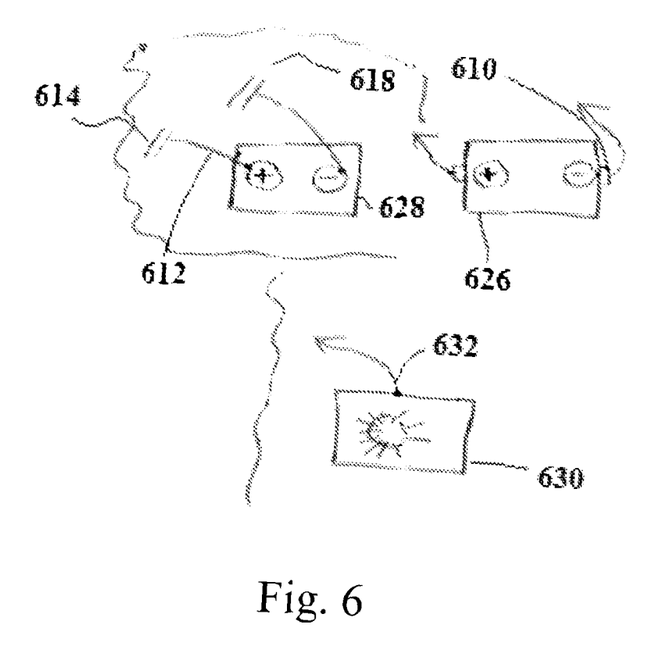
FIG. 6 illustrates an embodiment where a tactile sensory relay is mounted to the user's face.

In one embodiment of the disclosure the users face may be fitted by an output device, 610, connected, 612, to a sensor relay, 614. The sensor relay can in some embodiments detect tactile information including but not limited to any information on the user's sweat secretions. For instance the sensor relay's tactile sensor may detect moisture. The sensor relay may then send a signal to a computer processor which analyzes the signal and may send a signal to the movement device to alter the user's velocity, or to the user through an output device making a suggestion to alter the user's velocity. Yet another variation could involve the sensor relay measuring the opening or closing of a sweat gland directly as detected by its tactile sensor designed to measure such movements (on a scale less than a $mm^2$).

Another variation could involve the sensor relay detecting pulse (in one variation being mounted to a vein and designed to detect movement of the vein), and send it to a processor which calculates the beats per minute ("bpm") and uses that bpm to determine the fatigue of the user. In such an embodiment the processor may perform a variety of functions, including but not limited to analyzing the user fatigue computed against a default or a user defined set point, and then sending a signal to either the movement device or to the output device to allow the user to decide whether to slow the device the user is utilizing, cease activity, or neither.

In another variation, the user may be fitted with an array of sensor relays including tactile sensors that may detect the user's: pulse (which may be measured by means including but not limited to measuring vibrations, caused from the beating of the users heart sending blood to the brain, or elsewhere, through the users arteries and veins, any one or more of which the sensor relay is attached to), brain activity (which may be measured by means including but not limited to a tactile sensor relay or sensor relays designed to detect the direct flow of current from the brain to any one or more points on the users scalp), sweat (which may be measured by means including but not limited to a tactile sensor measuring moisture detection or weight over a pre set threshold or both), or any combination thereof.

The sensor relay may then send the information it detects to a computer processor designed to analyze the information through a variety of means including but not limited to plotting the user's pulse, brain activity, sweat, or any combination therein over time. After analyzing this information against a default or user defined set point, the computer processor may send a signal to the movement device or an output device. A signal to the output device may prompt the decision maker (any user or observer) to alter the movement device's settings, including but not limited to its incline, resistance, pressure, height, velocity, acceleration, or jerk based on those detections, whereas a signal to the movement device would cause said device to automatically adjust its settings.

In other variations the Signal Relay may be attached to the users nerve cells and detect variations through a variety of means, including but not limited to detecting voltage in a range from −70 mV to 30 mV (+/−15 mV) or instead measure the total displacement out of 100 mV (+/−10 mV), or any combination therein, sending that information to a computer processor which correlates the information against the users learning progress over time. The computer processor can then calculate the learning over time by any number of means, including but not limited to measuring the number of pages the user scrolls per minute, the average speed in which they answer questions over a given period of time, the number of questions which they answer correctly or any variation of responses to learning, entertainment, or other processing activity.

Alternatively the computer processor can send a signal to an output device to provide feedback, allowing the user to control the velocity of the device they are using, their own speed, adjust the device they are using, or adjust their own position, breathing, or any other control factors. Control Factors are any factor related to the user that can be monitored including but not limited to those such as breathing rate or pulse. The computer processor can also control or provide feedback to the output device or media device allowing the user to control the media feed rate based on that information or other nerve activity (including but not limited to detecting current or voltage from automatic nerves, central nerves, or cranial nerves to measure proper functionality according to predefined set points or user defined set points, and determining if the current or voltage from those nerves begins to fall outside of that range, to send a signal to the device for an emergency stop, set off an alarm or send an emergency signal to an observer).

The media feed rate is the rate at which a user is fed material, including but not limited to educational materials such as readings or lectures, entertainment materials such as television or videogames, or user controlled materials which can be downloaded or installed into the media device's processor through a number of means, including but not limited to USB, CD, internet or any combination therein. This can be either controlled by the user's actions, including but not limited to the user turning the page in a book, scrolling down a personal tablet, or changing the slide on a computer slide show; or processor controlled by the actions of a processor, including but not limited to automatically moving the digital image of an electronic display (such as scrolling or turning the page in an electronic book or website), changing the audio content to a song with a faster or slower pace accordingly, or pausing an entertainment movie until the user reaches their preset comfort level threshold.

In certain embodiments this sensor relay, 614, can also be fitted with an audio relay, 618, designed to send signals to the user for them to process including but not limited to verbal commands, beeps, or music related to their performance. In other embodiments the sensor relay may be directly powered by a variety of sources including but not limited to an external battery, 626. In other embodiments, extensions of the sensor relay may be powered by a variety of sources including but not limited to an external battery, 628. In other embodiments the sensor relay or its external rechargeable battery may be wired to any source of energy, including but not limited to a solar panel, 630, wind turbine, electrical outlet, or any combination thereof, and send energy, 632, back to the system.

Figure 7:
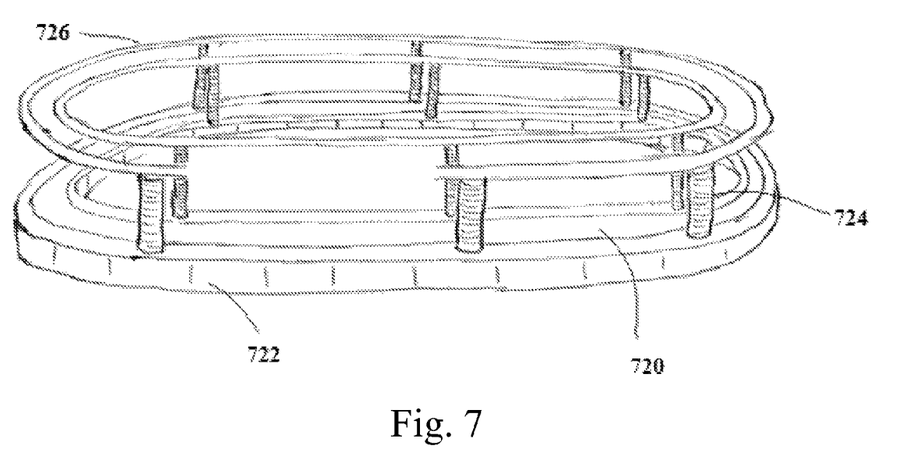
FIG. 7 illustrates a detailed orthogonal view of an embodiment comprising a circular treadmill which may be a component of the disclosure.

In some embodiments of the disclosure the device may be a track, 720, on top of a circular or an ellipsoidal treadmill, 722, wherein the user would move in a continuous pattern. In certain embodiments this device may include supports, 724, for handle bars, 726, which may be used for a variety of purposes, including but not limited to guiding the user as they traverse the track through the use of their body, hands, or any part of their body and the handle bars.

Figure 8:
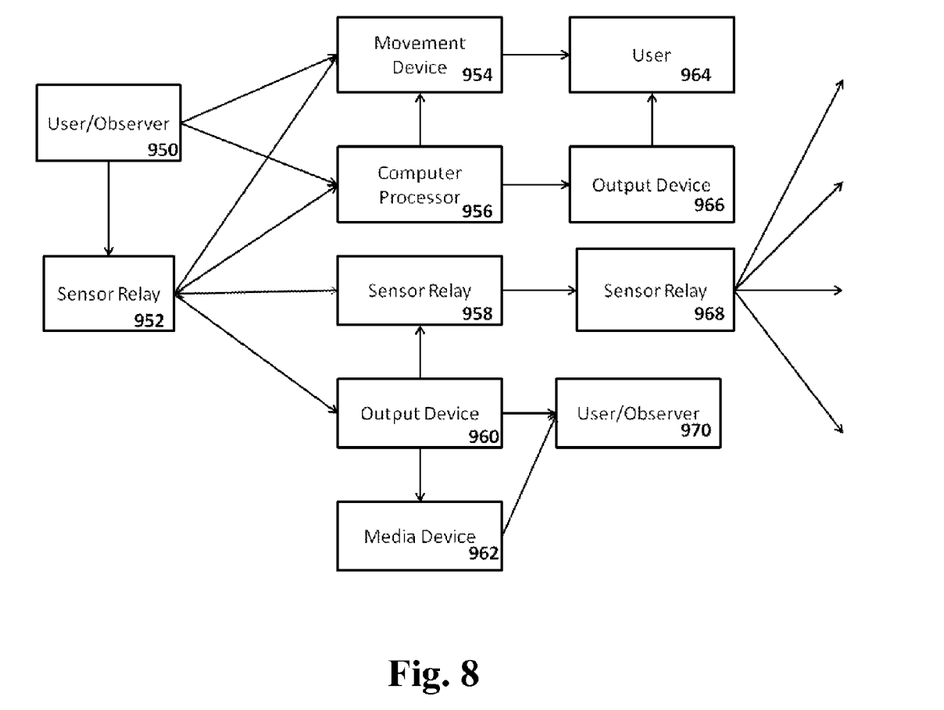
FIG. 8 illustrates a flowchart detailing a method of the disclosure by showing the flow in which users, observers, sensor relays, computer processors, output devices, media devices, and movement devices may act on one another.

The disclosure itself may involve any number of users or observers, 950, acting on sensor relays, 952, in any number of ways, which may in turn act on any number of movement devices, 954, computer processors, 956, other sensor relays, 958, output devices, 960, or media devices, 962.

Whereas a movement device may only act on any user, 964, the computer processor may act on either the movement device, or an output device, 966. The sensor relay may act on another sensor relay, 968, which may in turn act on any number of movement devices, computer processors, sensor relays, or output devices. The output device may act on a sensor relay, a media device, or a user or observer, 970.

It is understood that the various preferred embodiments are shown and described above to illustrate different possible features of the invention and the varying ways in which these features may be combined. Apart from combining the different features of the above embodiments in varying ways, other modifications are also considered to be within the scope of the invention.

The invention is not intended to be limited to the preferred embodiments described above, but rather is intended to be limited only by the claims set out below. Thus, the invention encompasses all alternate embodiments that fall literally or equivalently within the scope of these claims.

We claim:

1. A method of receiving sensory feedback while moving involving:
   one or more sensor relays;
   any number of output devices;
   any number of movement devices; and
   one or more computer processors that:
   receive a signal from any of the one or more sensor relays, detecting the information related to the user;
   analyze the detected information against one or more default or user defined set points;
   and either:
   send a signal to any of the output devices, instructing the decision maker with feedback related to one or more control factors measured against one or more set points;
   or
   send a signal to any of the movement devices, controlling said movement devices based on said analysis.

2. The method described in claim 1 wherein the user controls, is educated by, or is entertained by a media device.

3. The method described in claim 1 further comprising a moving walkway in a room for use by multiple users.

4. An apparatus comprising:
   one or more sensor relays;
   and either:

one or more output devices;
or
one or more movement devices;
wherein said sensor relay may detect information related to one or more user control factors;
and
wherein said sensor relay may send one or more signals to one or more other sensor relays, output devices or movement devices;
said output devices translating and communicating said signals to a decision maker as measured against one or more default or user defined set points;
said movement devices altering based on said signal measured against one or more default or user defined set points;
or
said other sensor relays detecting information related to the user and sending a signal to any of the one or more other sensor relays, output devices, or movement devices, or relaying the signal sent to it, to one or more other sensor relays, output devices, or movement devices measured against one or more default or user defined set points.

5. An apparatus as described in claim 4 further comprising one or more computer processors;
wherein said sensor relays may detect information related to the user;
wherein said sensor relay may send one or more signals to any of the one or more computer processors;
said computer processors may then analyze the detected information against any number of default or user defined set points;
and either:
send a signal to any of the output devices, instructing the decision maker;
or
send a signal to any of the movement devices, controlling said movement devices.

6. An apparatus as described in claim 5, further comprising
one or more of output devices;
and
one or more movement devices.

7. The method described in claim 5 further comprising a moving walkway in a room for use by multiple users.

8. The method described in claim 5 wherein feedback from said output device allows the user to alter the media device
or
feedback from said computer processor is sent to the media device, thereby automatically altering it.

9. A method described in claim 8 wherein one or more output devices is a headset comprising the steps of: having one or more users in motion through the use of one or more movement devices, further assisted through the use of one or more sensor relays, controlling one or more output devices presenting the users with content while in motion, one or more movement devices, or one or more computer processors or presenting the user with feedback related to one or more control factors measured against one or more set points.

10. An apparatus as described in claim 4, further comprising:
one or more of output devices;
and
one or more movement devices.

11. The apparatus described in claim 10 further comprising:
a straight treadmill which responds to one or more signals sent to it.

12. The apparatus described in claim 10 further comprising:
a circular treadmill which responds to one or more signals sent to it.

13. The apparatus described in claim 10 comprising a treadmill that uses a combination of solar power and battery power to maintain a default speed.

14. The apparatus described in claim 10 wherein
Said computer processors send signals controlling said media devices.

15. The apparatus described in claim 4 further comprising:
a media device.

16. The apparatus described in claim 4 further comprising a
standard treadmill.

17. The apparatus described in claim 4 further comprising:
a circular treadmill which responds to signals sent to any of the movement devices.

18. The apparatus described in claim 4 comprising a treadmill that uses a combination of solar power and battery power to maintain a default speed.

* * * * *

UNITED STATES PATENT AND TRADEMARK OFFICE
CERTIFICATE OF CORRECTION

PATENT NO. : 9,818,285 B2  
APPLICATION NO. : 14/217508  
DATED : November 14, 2017  
INVENTOR(S) : James Clarke and Chiedo Ohanyerenwa Page 1 of 1

It is certified that error appears in the above-identified patent and that said Letters Patent is hereby corrected as shown below:

In the Claims

In Column 9, Line 44, replace "The method..." with "The apparatus..."

In Column 9, Line 46, replace "The method..." with "The apparatus..."

In Column 10, Line 5, replace "A method..." with "The apparatus..."

Signed and Sealed this  
Twenty-second Day of August, 2023

Katherine Kelly Vidal  
*Director of the United States Patent and Trademark Office*